United States Patent [19]

Bradley et al.

[11] Patent Number: 5,939,065
[45] Date of Patent: Aug. 17, 1999

[54] **MYCOINSECTICIDE ACTIVITY AGAINST GRASSHOPPERS PRODUCED BY *BEAUVERIA BASSIANA***

[75] Inventors: Clifford A. Bradley; Pauline P. Wood; James Britton, all of Butte, Mont.

[73] Assignee: Mycotech Corporation, Butte, Mont.

[21] Appl. No.: 08/840,417

[22] Filed: Apr. 29, 1997

Related U.S. Application Data

[63] Continuation of application No. 08/430,262, Apr. 28, 1995, abandoned, which is a continuation of application No. 08/135,209, Oct. 12, 1993, abandoned.

[51] Int. Cl.$^6$ .............................. A01N 63/00; C12N 1/14
[52] U.S. Cl. ...................................... 424/93.5; 435/254.1
[58] Field of Search ........................ 424/93.5; 435/254.1

[56] References Cited

U.S. PATENT DOCUMENTS

| | | | |
|---|---|---|---|
| 3,911,110 | 10/1975 | Smirnoff | 424/93 |
| 4,401,762 | 8/1983 | Tellier et al. | 435/243 |
| 4,695,462 | 9/1987 | Barnes et al. | 424/195.1 |
| 4,925,663 | 5/1990 | Stimac | 424/93 Q |
| 5,089,530 | 2/1992 | Tsipouras et al. | 514/682 |
| 5,242,907 | 9/1993 | Dawson | 514/65 |
| 5,413,784 | 5/1995 | Wright et al. | 424/935 |
| 5,418,164 | 5/1995 | Anderson et al. | 435/254.1 |

FOREIGN PATENT DOCUMENTS

54766/86  9/1986  Australia .

OTHER PUBLICATIONS

Johnson et al., "Mortality of Grasshoppers (Orthoptera: Acrididae) Inoculated with a Canadian Isolate of the Fungus *Verticillium lecanii*" *Journal of Invertebrate Pathology*, vol. 52, pp. 335–342, (1988).

Khachatourians G. G. "Virulence of Five Beauveria strains, *Paecilomyces farinosus*, and *Verticillium lecanii* against the Migratory Grasshopper, *Melanoplus sanguinipes*" *Journal of Invertebrate Pathology*, vol. 59, pp. 212–214, (1992).

Marcandier et al., "Susceptibility of the Migratory Grasshopper, *Melanoplus sanguinipes* (Fab.) (Orthoptera: Acrididae), to *Beauveria bassiana* (bals.) Vuillemin (Hyphomycete): Influence of Relative Humidity" *The Canadian Entomologist* Oct., vol. 119, pp. 901–907, (1987).

Moore et al., "Isolation of *Aspergillus parasiticus* speare and *Beauveria bassiana* (bals.) Vuillemin from melanopline Grasshoppers (Orthoptera: Acrididae) and Demonstration of their Pathogenicity in *Melanoplus sanguinipes* (Fabricius)" *The Canadian Entomologist* Nov., vol. 120, pp. 989–991, (1988).

Prior et al., "Biological control of locusts: the potential for the exploitation of pathogens" *FAO Plant Prot. Bull.*, vol. 37, No. 1, pp. 37–48, (1989).

*Primary Examiner*—Irene Marx
*Attorney, Agent, or Firm*—Lahive & Cockfield LLP; Elizabeth A. Hanley; Linda M. Chinn

[57] ABSTRACT

An entomopathogenic fungus virulent against insects of the grasshopper family is described. The entomopathogenic fungus is a strain *Beauveria bassiana*. Also, formulations that include the entomopathogenic fungus are described. These formulations can be delivered to grasshopper-infested areas by land or by air. In addition, methods of killing an insect of the grasshopper family using the aforementioned formulation and baits and traps for killing an insect of the grasshopper family containing the formulation are described.

4 Claims, 11 Drawing Sheets

Fig. 1

Bioassay of Beauveria bassiana in oil or clay formulations against third and fourth instar nymphs of Oedaleus senegalensis in Cape Verde.

Topical Bioassay
B. bassiana GHA vs. M. sanguinipes

Spores per Grasshopper
- 100
- 390
- 1560
- 6250
- 25000
- 100000

Fig. 2

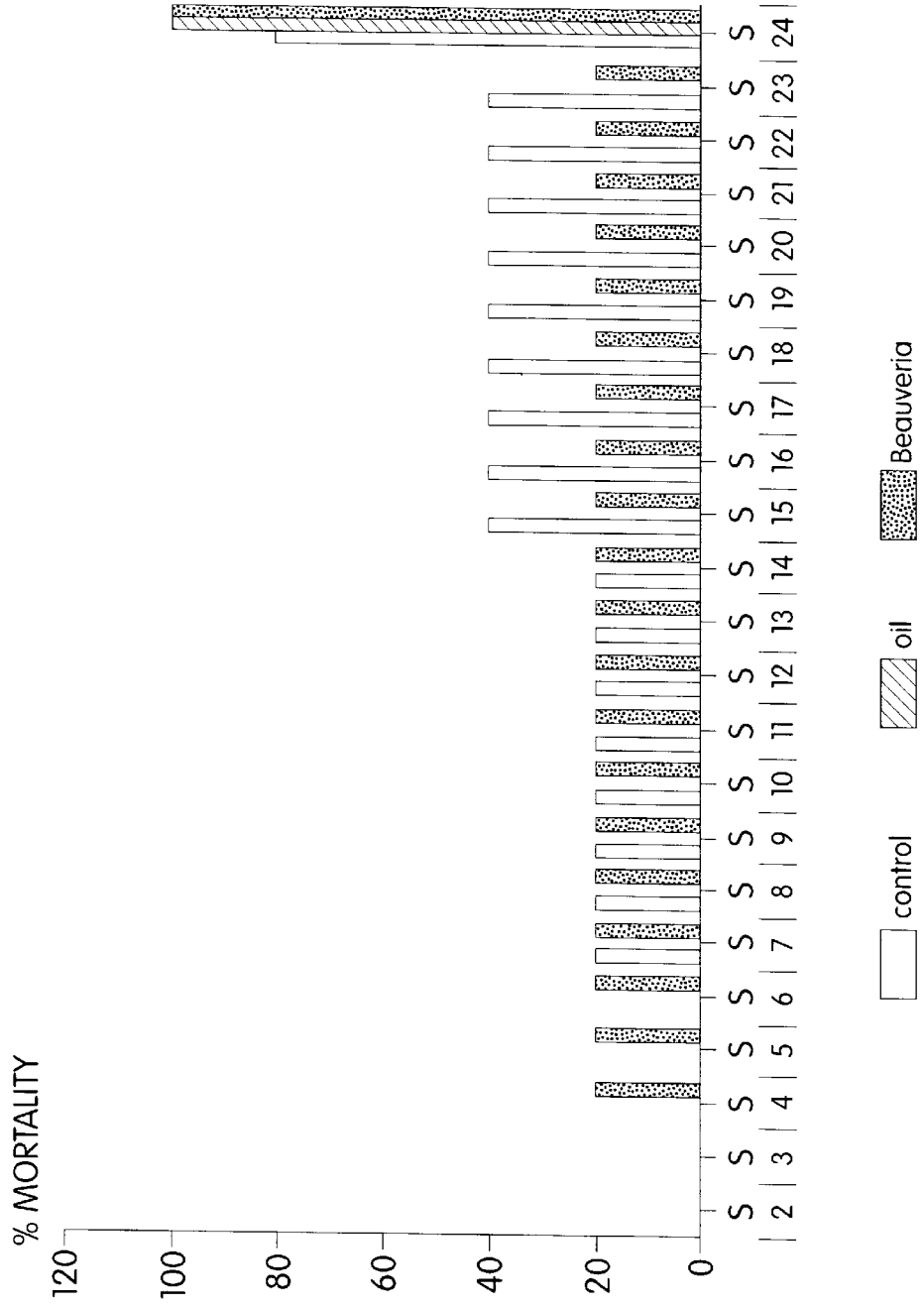

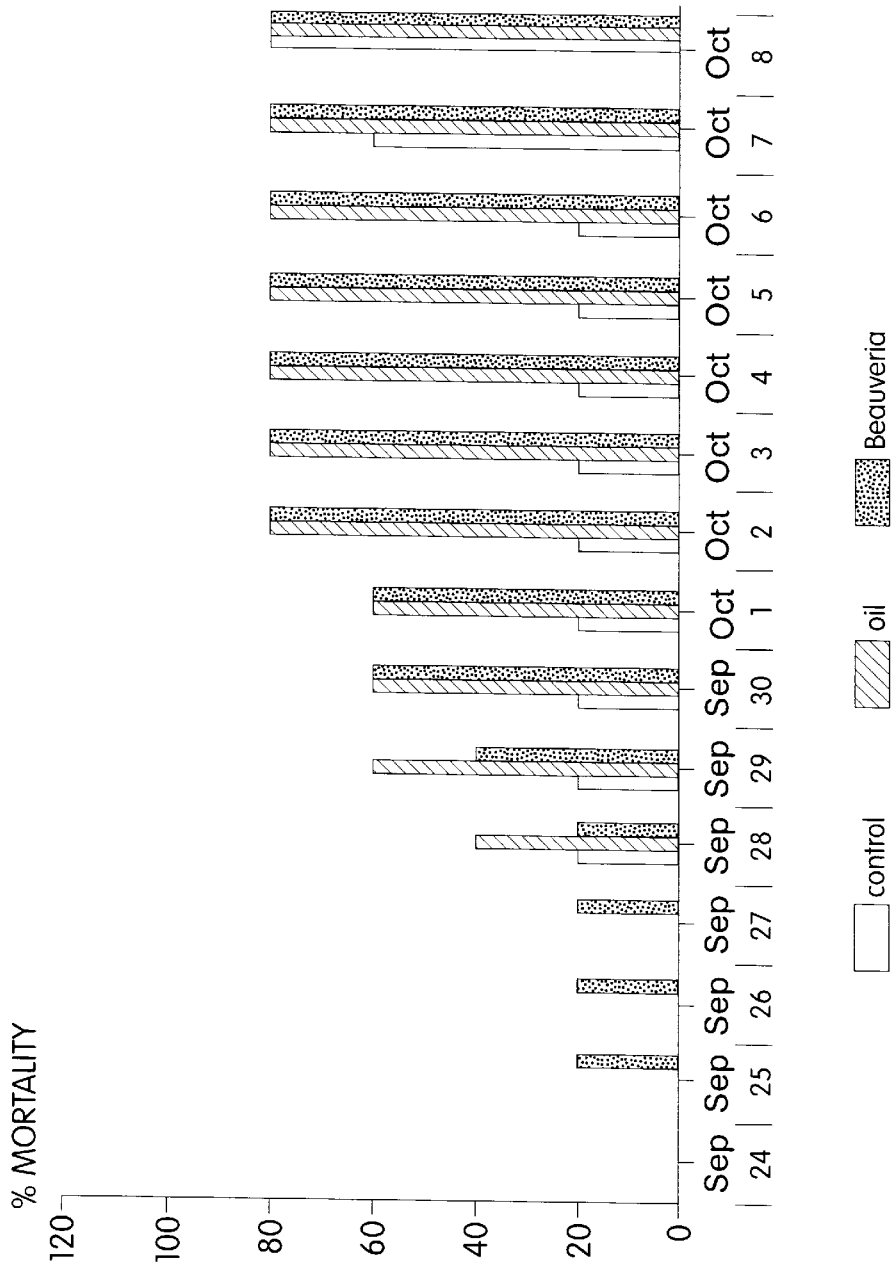

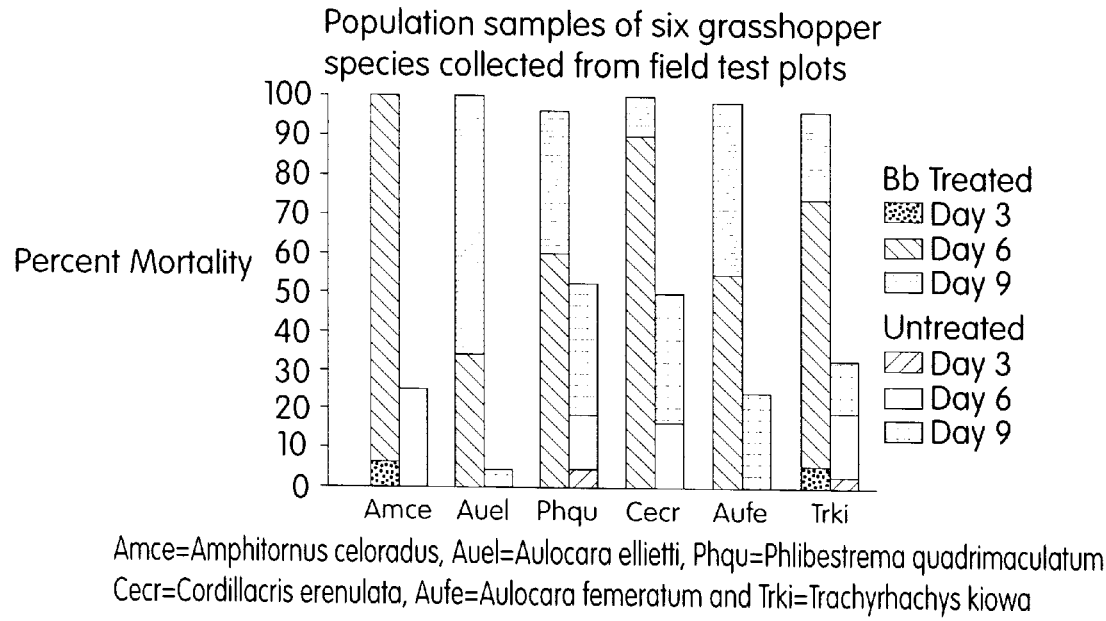
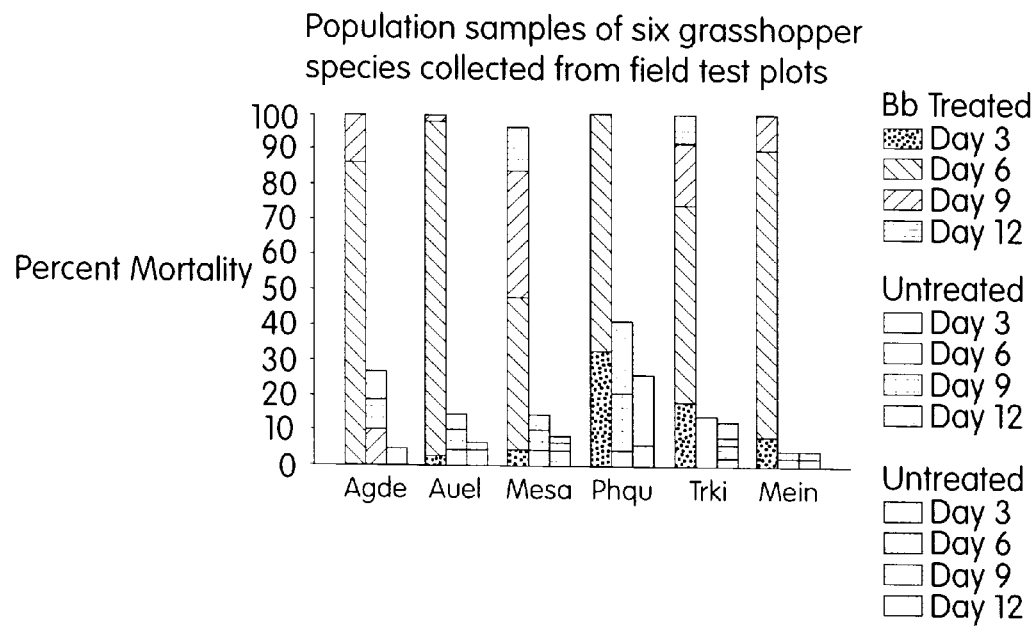
Fig. 5

Six species of grasshoppers were treated aerially Beauveria bassiana and held on native rangeland in cages Percent Mortality vs Amce, Auel, Phqu, Cecr, Aufe, Trki
Legend: Bb Trt, Untrt.

Amce=Amphitornus celoradus, Auel=Aulocara ellietti, Phqu=Phlibestrema quadrimaculatum
Cecr=Cordillacris erenulata, Aufe=Aulocara femeratum and Trki=Trachyrhachys kiowa Six species of grasshoppers were treated aerially Beauveria bassiana and held on native rangeland in cages Percent Mortality vs Agde, Auel, Mesa, Phqu, Trki, Mein
Legend: Bb Trt, Untrt., Oil only Agde= Agencetattis decrum, Auel= Aulocara elliotti, Meaz=Malanopus sanguinipes, Phqu= Phlibastroma quadrimaculatum, Trik= Trachyrhacgys kiowa Mien= Melanoplus infantilis

Fig. 6

MYCOINSECTICIDE ACTIVITY AGAINST GRASSHOPPERS PRODUCED BY *BEAUVERIA BASSIANA*

RELATED APPLICATIONS

This application is a continuation of application Ser. No. 08/135,209 filed on Oct. 12, 1993 Entitled: MYCOINSECTICIDES AGAINST AN INSECT OF THE GRASSHOPPER FAMILY and Ser. No. 08/430,262 filed on Apr. 28, 1995 Entitled: MYCOINSECTICIDES AGAINST AN INSECT OF THE GRASSHOPPPER FAMILY now both abandoned. The contents of all of the aforementioned applications are expressly incorporated by reference.

This application is related to applications entitled "Formulations of Entomopathogenic Fungi for Use as Biological Insecticides" (U.S. Ser. No. 08/134,563), now abandoned and "A Solid Culture Substrate Including Barley"(U.S. Ser. No. 08/134,849), now abandoned, filed on even date herewith, the contents of each of the aforementioned applications are hereby expressly incorporated.

BACKGROUND OF THE INVENTION

Currently, there are several methods of controlling economically important pests such as grasshoppers and locusts. These methods fall into two broad categories—chemical and biological. Chemical methods are the most commonly used and entail the use of chemical pesticides. However, chemical pesticides can pose risks to human health and cause environmental damage due to adverse effects on non-target insects and other animals. Also, chemical pesticides used for grasshopper control are non-selective and kill other, beneficial insects in sprayed areas. In short, chemical pesticides can kill pollinating insects, adversely affecting plant life or can upset insect population balances by killing predators or parasitic insects that naturally control the insects population.

Biological methods of controlling economically-important pests have become increasingly attractive as a less ecologically-destructive way of dealing with these insects. Biological methods exploit an insect's natural enemies and include using insect parasitoids, predators, and pathogens. Of the various ways to use an insect's natural enemies as biological control agents for that insect, one of the most common is mass multiplying pathogens such as bacteria or fungi and applying them to an affected area as a biopesticide. Organisms which have been under investigation as potential biopesticides include viruses, nematodes, protozoa, bacteria and fungi.

Biopesticides can be very expensive to raise and can be difficult to deliver effectively to the target insect. To date, bacteria is a commonly used form of biopesticide. For example, strains of the bacteria *Bacillus thuringiensis* have been used against susceptible Lepidoptera, Diptera, and Coleoptera. Fungi such as Metarhizium and Beauveria are virulent against a wide range of insects and can be economically mass produced according to methods described in the patent application entitled "A Solid Culture Substrate Including Barley" filed even date herewith, the contents of which are expressly incorporated herein. However, Prior and Greathead (*FAO Plant Prot. Bull.* 37:37–48 (1989)) state that "[a] pathogen such as Beauveria will kill a target insect only in an unfavourable climate, such as the majority of locust outbreak areas, if it either hits the insect directly or contacts it rapidly after application and before it is inactivated by UV, high temperature, or low [relative humidity]."

SUMMARY OF THE INVENTION

This invention provides an entomopathogenic fungus which is virulent against insects of the grasshopper family without significantly harming non-target insects. The entomopathogenic fungus further is non-toxic to consumers and/or users and also does not detrimentally affect vegetation. One embodiment of the claimed entomopathogenic fungus is a specific isolate of *Beauveria bassiana*.

Certain species of fungi are well known pathogens of insects. One embodiment of this invention is a specific isolate of the entomopathogenic fungus, *Beauveria bassiana*. This isolate combines characteristics which make it particularly well suited to the control of grasshopper including locust. These characteristics include:

- a high degree of virulence toward grasshoppers
- efficient production of stable, infective conidia which comprise the active ingredient of mycoinsecticide
- conidia which are comparatively resistant to damage from elevated temperatures and which are stable in storage
- limited infectivity or pathogenicity to insects other than grasshopper and locust
- no adverse affects on vertebrates.

Therefore, the entomopathogenic fungus of the present invention is effective against grasshoppers, can be stored and transported in commercial distribution channels without special handling and has fewer adverse effects on non-target species, including humans, and the environment than chemical pesticides.

The present invention also provides formulations including the entomopathogenic fungus which are easy to deliver to grasshopper-infested target areas in that the formulations can be delivered by land or by air, for example, using a spraying device from an airplane. In addition, a small volume of the formulation is capable of covering a large area of land. This invention also provides entomopathogenic formulations for incorporation into a trap. The formulations comprise the entomopathogenic strain of *Beauveria bassiana* in combination with a solid substrate, an oil, an emulsion, or a suspension. Formulations of the present invention that incorporate conidia of the claimed entomopathogenic fungus remain virulent in the presence of ultraviolet radiation and low relative humidity.

Other aspects of this invention include methods of killing an insect of the grasshopper family using the forementioned suspensions and/or formulations and baits and traps for killing an insect of the grasshopper family containing the formulation. The traps also can contain lures for attracting the insects to the trap.

BRIEF DESCRIPTION OF THE DRAWINGS

FIG. 1 is graphs showing mortality results of a bioassay for virulence of BbGHA1991 against *Oedaleus senegalensis*.

FIG. 2 is a graph showing mortality results of a bioassay for virulence of BbGHA1991 against *Melanoplus sanguinipes*.

FIGS. 3a, 3b and 3c are bar graphs showing results of three tests of BbGHA1991 against a non-target insect, *Nicrophorus marginatas*.

FIG. 5 is bar graphs showing mortality results of six grasshopper species collected from field test plots for two separate tests after application with BbGHA1991.

FIG. 6 is bar graphs showing mortality results of grasshoppers treated aerially with BbGHA1991 and held on native rangeland in cages for two separate tests.

DETAILED DESCRIPTION

Figure 3B:
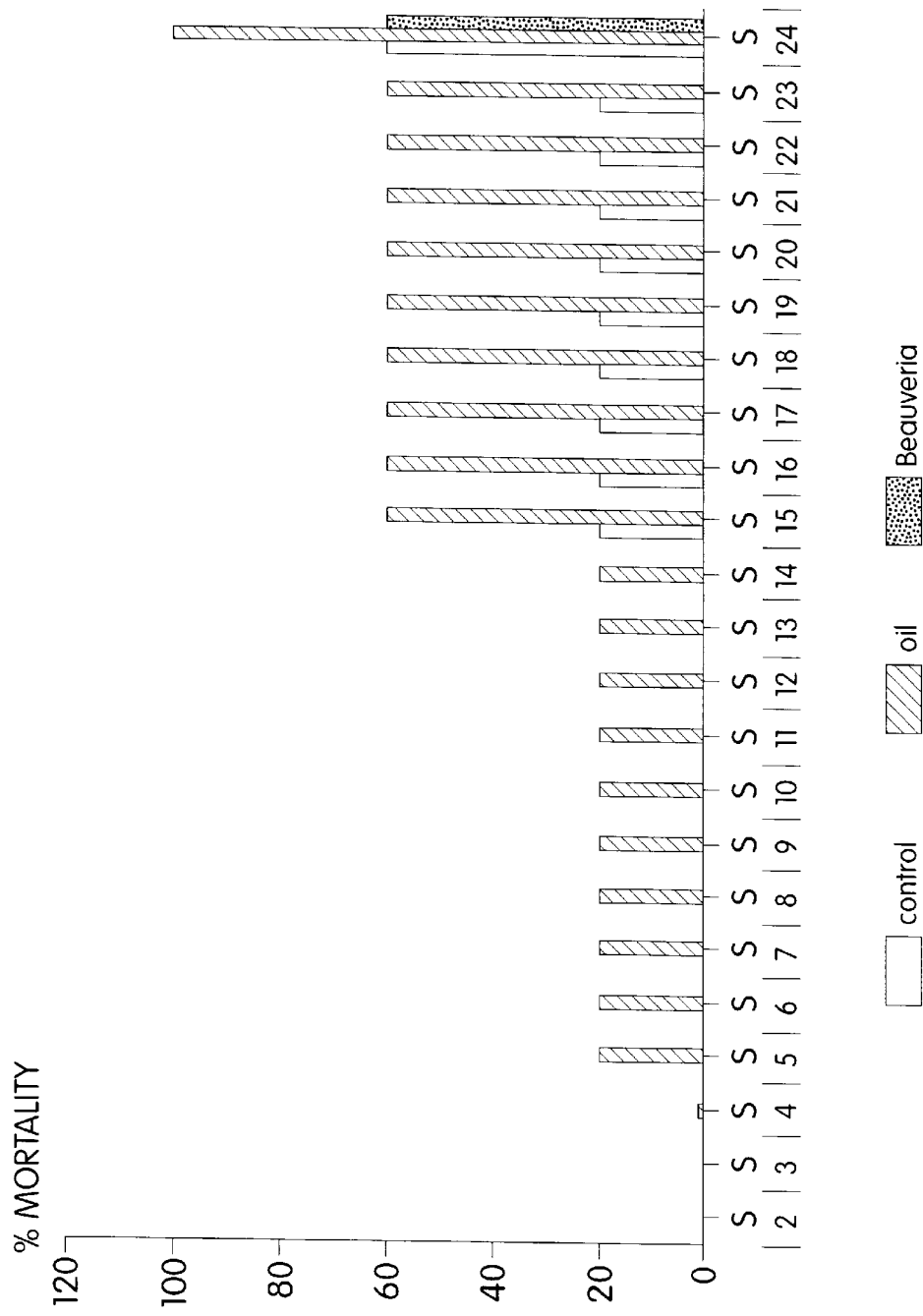

The present invention pertains to an entomopathogenic fungus to be used for the extermination of insects of the grasshopper family (Acrididae). The entomopathogenic fungus is an isolate of *Beauveria bassiana* which is virulent against an insect of the grasshopper family.

The language "entomopathogenic fungus" means a fungus which is capable of killing an insect. Such a fungus is considered a mycopesticide. Entomopathogenic fungi include those strains or isolates of fungal species in the class Hyphomycetes which possess characteristics allowing them to be virulent against insects. These characteristics include formation of stable infective conidia. An effective entomopathogenic fungus preferably is lethal for target insects but less harmful for non-target insects. Also, the entomopathogenic fungus preferably does not harm vegetation or animals who might come in contact with it.

The language "fungus of the class Deuteromycete" is intended to include fungi that are recognized in the art as being Deuteromycete fungi. Deuteromycete fungi are fungi of the subdivision Deuteromycotina. There are two classes of Deuteromycete—Hyphomycetes and Coelomycetes. Hyphomycetes fungi generally produce conidia. Deuteromycete fungi include fungi of the genera Beauveria, Metarhizium, Paecilomyces, Tolypocladium, Aspergillus, Culicinonyces, Nomuraea, Sorosporella, and Hirsutella. Examples of species of Deuteromycete fungi include *Beauveria bassiana, Metarhizium flavoviride, Metarhizium anisopliae, Paecilomyces fumusoroseus, Paecilomyces farinosus,* and *Nomuraea rileyi.*

The language "a strain of *Beauveria bassiana*" is intended to include strains or isolates of *Beauveria bassiana* which possess characteristics allowing them to be virulent against an insect of the grasshopper family. Strains of *Beauveria bassiana* typically produce high concentrations of stable conidia that are infective by insect cuticle penetration, producing infection with obvious morbidity in two to four days and insect death at three to ten days. An example of an isolate of *Beauveria bassiana* is BbGHA1991, which has been deposited with the American Type Culture Collection (ATCC) (Manassas, VA.) on Oct. 11, 1993, under the terms of the Budapest Treaty. ATCC Accession number 74250 has been assigned to the deposit"

The language "BbGHA1991" is intended to include an isolate of *Beauveria bassiana* possessing the following characteristics:

Virulence: Dose required for infection as measured by $LD_{50}$ or $LD_{90}$ in laboratory bioassay is low enough to be economically and technically feasible for use as mycopesticide, generally, an $LD_{50}$ at seven to ten days post-exposure of less than 100,000 viable conidia per insect. $LD_{50}$ of BbGHA1991 is 1,000–20,000 conidia per insect depending on insect species and development stage. Virulent to a wide range of acridid species.

Infectivity: Infective to the insect under field conditions of grasshopper habitats, that is relatively high ambient temperature and low relative humidity. Infects via direct contact with spray or by grasshoppers contacting spores on native vegetation.

High conidia production: Produces high level of conidia making production economical.

Stability: Conidia are comparatively tolerant of short term exposure to high temperatures (greater than 30° C., up to 50° C.) and stable in storage for extended periods under ambient conditions (25° C.).

Host Specific: Strain is not pathogenic or toxic to vertebrates, is not infective in or produces toxins harmful to vertebrates. Strain is not highly virulent to non-target insects.

BbGHA1991 is a highly virulent strain of fungus with respect to a wide range of species of insects of the grasshopper family. The lethal dose which can kill 50% of the insects with which the strain comes in contact (hereinafter called $LD_{50}$) of BbGHA1991 in the laboratory is 20,000 to less than 1000 conidia/grasshopper. The BbGHA1991 strain of *Beauveria bassiana* has greater production efficiency and temperature stability than other Beauveria strains of comparable virulence. Enhanced temperature stability of the strain as both a dry powder and as an oil suspension allows for transport to and longer storage in hot climates. In addition, BbGHA1991 has only limited effects on non-target insects compared to other isolates of *Beauveria bassiana* virulent to Acrididae species. BbGHA1991 was isolated from a strain isolated from an infected corn root worm, *Diabrotica undecimpunctata.*

The language "grasshopper" includes insects recognized by those of skill in the art as grasshoppers, locusts and crickets. This includes insects in the order Orthoptera, suborders Caelifera and Ensifera. Representative families include, but are not limited to Acrididae, (grasshoppers and locust), Tettigoniidae (long horned grasshoppers), Gryllidae (Crickets) and Cryllotalpidae (mole crickets). Examples of important species include: *Melanoplus sanguinipes, Aulocara elliotti, Camnula pellucida, Oedaleus senegalensis, Locusta migratoria, Schistocerca gregaria* and *Scapteriscus vicinus.*

The phrase "without significantly harming non-target insects" means that insects not of the grasshopper family are not infected and killed by the entomopathogenic fungus at dose rates which kill grasshoppers. It is important that non-target insects are not significantly harmed by the entomopathogenic fungus under conditions which the fungus is effective in the field as a mycoinsecticide for grasshopper control. Elimination of non-target species can remove insect predators and parasites adversely effecting ecological balances - resulting in potential outbreaks of other pest species or exacerbated outbreaks of acridids. Non-specific pesticides (whether chemical or biological) can also eliminate pollinating species, adversely affecting plant reproduction.

The term "$LD_{50}$" means the median lethal dose of the entomopathogenic fungus which will kill half the insects receiving that dose. Typically, the $LD_{50}$ of a fungus is measured in number of conidia. The $LD_{50}$ of a substance such as a fungus is determined with respect to a group of subjects in a laboratory bioassay. For example, serial dilutions of a fungus are made and a known amount of each dilution is applied individually in replicates to a group of grasshoppers. The grasshoppers are then fed and monitored daily for mortality. The data acquired is then analyzed by known methods to determine the $LD_{50}$ of the fungus with respect to grasshoppers. The assay used to measure $LD_{50}$ of entomopathogenic fungi of the present invention is described in detail in Example 5. The $LD_{50}$ values of the present invention are calculated as conidia per insect.

The term "conidia" is art-recognized and intended to include asexual spores characteristic of many fungi including the claimed entomopathogenic fungus. Conidia of a fungus can be counted and used as units of measure of the fungus, for example, with respect to viability and $LD_{50}$.

The present invention also pertains to formulations containing conidia of the claimed fungus. Formulations include conidia of the claimed entomopathogenic fungus in combination with a carrier. The carrier can be a solid substrate, an oil, an emulsion, or a suspension. The formulation can be applied to an affected geographical area by aerial application or by spraying from the ground.

The language "entomopathogenic formulation" is intended to include a mixture of conidia of an entomopathogen such as BbGHA1991 and a carrier. The carrier is a substance capable of dispensing conidia of the fungus appropriately without affecting the fungus' ability to perform its intended function. Carriers include solid substrates, oils, emulsions, and suspensions. Entomopathogenic formulations that can be used in the present invention are described in detail in the patent application entitled "Formulations of Entomopathogenic Fungi For Use As Biological Insecticides," filed on even date herewith, the contents of which are expressly incorporated herein.

The language "a solid substrate" is intended to include solid materials capable of supporting the growth of a fungus. The solid support can contain nutrients or has the ability to hold media containing nutrients. Examples include grain (wheat, rice, barley), starch or flour coated onto inert supports (such as plastic or metal shapes), liquid nutrient media sorbed into porous materials such as clay or ceramic beads, cellulosic materials such as wheat bran, rice hulls, wood chips, etc. Solid substrates are useful for growing cultures of *Beauveria bassiana* and for baits or traps as described below.

The term "oil" is intended to include substances which are unctuous, viscous liquids at ordinary temperatures. Oils can be derived from either petroleum or from vegetables. Oils include light paraffinic oils such as SUNSPRAY® 6N, SUNSPRAY® 6E, or SUNSPRAY® 7E as well as other petroleum-based oils and vegetable oils such as those derived from corn, cottonseed, soy beans, palm or coconut, rape seed, and sunflower seed. In addition, conidia are killed by exposure to sunlight, particularly ultraviolet wavelengths. Oils preferably include those that can protect entomopathogenic fungal conidia from harmful ultraviolet radiation. Formulations which protect conidia from sunlight damage are advantageous in increasing persistence of conidia in the field after spraying. Conidia are also killed by exposure to elevated temperatures. Oils included are those that do not adversely affect, or preferably those which enhance, conidia stability.

The term "emulsion" is intended to include mixtures of two liquids not mutually soluble which are capable of suspending the conidia of the entomopathogenic fungus. Emulsions include mixtures of oil and water. In an oil and water emulsion, the oil aids in suspension of the hydrophobic conidia and allows for high volume dispersion of the conidia of the fungus.

The term "suspension" is intended to include a solid substance in which a particulate form is mixed with a fluid but which remains undissolved. Suspensions include those where clay is suspended in water and conidia are suspended in water or oil. In clay/water suspensions, the clay helps the hydrophobic conidia to be suspended in water for greater dispersion.

The term "clay" is intended to include natural earthy materials that are plastic when wet and can act as a carrier in suspension for a fungus. Clays within the scope of this invention include attapulgite clay, clay, kaolin, and bentonite.

Conidia of *B. bassiana* are hydrophobic and suspend well in oil. Oil/conidia suspensions can be applied as low volume sprays. Dry conidia powder can be suspended in water for application. Compatible detergents and clay aid suspension of hydrophobic conidia in water. Emulsions of conidia in oil and water can be used for high volume application. Conidia suspended in oil, dry conidia powder or dry mixtures of conidia and clay are stable and have a long shelf life. A suspension of conidia in water must be used within one day as conidia germinate and become non-infective or die. Conidia suspended in oil are stable in storage and with transitory exposure up to 50° C., such as might occur in transport or in an airplane spray tank during application. Formulations suitable for low or ultra-low volume aerial application are an advantage in use of an entomopathogenic fungus for grasshopper control for economical application to large areas or over rough terrain where ground application is not feasible. In addition, water can be added to the conidia/oil formulation to form an emulsion for high volume application and the emulsion can be stored for several days prior to use.

Next, the present invention provides methods of killing insects of the grasshopper family using the aforementioned formulations. The formulation is applied to an affected geographical area by either land or air.

The language "an affected geographical area" is intended to include a parcel or portion of land which has insects of the grasshopper family present on that land. Affected geographical areas include those areas which contain large numbers of insects of the grasshopper family that cause damage to vegetation or crops.

The term "applying" is intended to include methods of bringing the entomopathogenic fungus in contact, either externally or internally, with an insect of the grasshopper family. Application includes direct application of the claimed fungus to the insect as in topical administration. Application also includes spraying an affected geographical area with the claimed fungus in liquid suspension. In addition, application includes contact between the fungus and insect when the conidia are sprayed on vegetation or soil. The insect can contact the fungus as a result of walking on or feeding on sprayed foliage or walking on sprayed soil. The suspended fungus can be sprayed on the affected geographical area from the air such as from a low flying plane or from the ground such as by an individual with a tank sprayer.

The present invention also provides for the use of a formulation of conidia of the claimed fungus in a trap in combination with a lure which can attract an insect of the grasshopper family into the trap.

The term "trap" is intended to include devices used to lure an insect of the grasshopper family into a position where it will be exposed to or ingest a poison. A trap generally includes a lure which attracts the insect of the grasshopper family into the trap. Traps include containers which have openings that allow an insect to enter and be exposed to or ingest the claimed fungus.

The term "lure" is intended to include substances which will attract an insect of the grasshopper family and cause it to enter the trap. The lure can entice an insect of the grasshopper family into a place where it would not normally enter. Lures include pheromones, either natural or synthetic, and foodstuff such as lettuce or grass.

The term "pheromone" is intended to include chemical substances released by an insect that serve to influence the physiology or behavior of other members of the same species. Pheromones are often used in insect traps as an effective lure. Pheromones include those chemical substances released by insects of the grasshopper family.

The term "bait" is art-recognized. Typically, bait includes a mixture of an entomopathogenic fungus and a foodstuff. The foodstuff includes grain such as wheat bran, corn meal, and oatmeal.

The present invention also provides an entomopathogenic fungus that is a strain of a fungus of the class Deuteromycete, $1.0 \times 10^7$ conidia of which are non-toxic to a rat based on a bioassay conducted pursuant to U.S. EPA Subpart M guidelines, Section Series 152A-13 which are expressly incorporated herein by reference. In part, U.S. EPA guidelines provide guidance to makers of chemical and biological agents, including insecticides, as to acceptable limits of toxicity and provide standardized tests for determining toxicity.

The following invention is further illustrated by the following non-limiting examples. The contents of all cited copending applications, issued patents, and published references are hereby expressly incorporated by reference.

EXAMPLES

Materials and Methods
Strain History *Beauveria bassiana* GHA 1991

The strain of *Beauveria bassiana* designated BbGHA1991 was originally selected from screening studies and subsequently derived by infection and re-isolation from grasshoppers and locust. The original strain was obtained from the USDA collection of entomopathogenic fungi, Ithaca, N.Y. and designated ARSEF 201. ARSEF 201 was originally isolated in Oregon, USA, from an infected corn root worm, *Diabrotica undecimpunctata*.

ARSEF 201 was selected from a screening that compared a set of 25 isolates obtained from the USDA ARSEF collection and University researchers. Three of the *Beauveria bassiana* strains in their original screening were reported as isolated from grasshopper. These were ARSEF 32, 356, and 357. ARSEF 32 was the only isolate reported from grasshopper in the US. The others were from Australia.

Reisolation

The parent strain, designated 201C was used in a series of laboratory bioassays by INIDA in Cape Verde and Agriculture Canada, Lethbridge, Alberta. Grasshoppers killed in the bioassays were placed in a petri dish with a damp cotton ball for two to four days, causing conidia formation on the infected cadavers. Mycotech received conidiated cadavers of *Oedaleus senegalensis* from Cape Verde and of *Oedaleus senegalensis* and *Locusta Migratoria* from Ag Canada for reisolation.

Reisolations were made by transferring a conidiated piece of cadaver to a broth medium selective for *Beauveria bassiana* growth. Medium composition was as follows:

CSYE Dodine Broth 40 g/l glucose
10 g/l $KNO_3$
5 g/l $KH_2PO_4$
2 g/l $MgSO_4$
2 g/l Yeast Extract
0.5 g/l Dodine Fungicide (CYPREX 65W tradename for dodecylguanidine monoacetate, American Cyanamid Corp.)
0.05 g/l Tetracycline HCl
1.0 ml/l COMBIOTIC® (tradename for a streptomycin-pennicillin mixture) (Streptomycin, Penicillin Mixture, Pfizer Corp.)

After three to five days growth, an aliquot of the dodine broth culture was diluted 1:10,000 and the dilutions used to inoculate fresh dodine broth.

After two to three cycles of dilution and growth in dodine broth and when cultures appeared uniform, a final dilution transfer was made to broth without dodine and to Sabaroud's dextrose agar plates. Final broth cultures were used as inoculum for laboratory solid cultures. Agar plates were used as a check for uniformity of the culture. For two reisolations, a single colony from the final dilution plate was used as the source for starting broth inoculum cultures used to inoculate laboratory solid cultures.

Laboratory solid cultures were prepared by wetting 50 g of barley flakes with 50 ml of a nutrient solution containing 10 g/l $KNO_3$, 5 g/l $KH_2PO_4$, and 2 g/l $MgSO_4$.

Wetted barley was autoclaved for 20 minutes at 15 psi at 121° C., cooled, and inoculated with 10–15 ml of broth culture. Inoculated substrate was then transferred to a 12"× 1¼" ID sterile polycarbonate tube fitted with screw caps and tubing connectors. Culture tubes were then connected to air lines in a temperature-controlled rack and incubated at 25° C. with 5–20cc air per minute for eight to twelve days. At the end of the culture period, solid cultures were dried and conidia recovered by milling and screening.

Conidia concentration in the whole culture was determined by shaking a 5 g sample of culture in 50 or 100 ml of 0.1% TWEEN® 80 (tradename for polyoxyethylenesorbitan biological detergent) until barley kernels were washed free of culture, generally, ten minutes on a high speed wrist shaker. The wash was diluted as appropriate and counted on a hemocytometer. Concentration of conidia in recovered dry powder was determined by transferring a 0.1 g sample to 10 ml of 0.1 % TWEEN® (tradename for polyoxyethylenesorbitan biological detergent) in a tissue homogenizer tube. The suspension was homogenized for two minutes to disperse conidia. It was then further diluted as appropriate, generally to a final dilution of 1:10,000 from powder, and counted on a microscope hemocytometer. Whole dry culture or dry conidia powder was stored at 4° C. as a source for additional inoculum culture and for evaluation.

Example 1

Reisolate Virulence Comparisons; Selection of GHA

Three laboratory solid cultures of each of six reisolates (two from Lethbridge, four from Cape Verde grasshoppers) and the parent strain 201C. were prepared and conidia powder pooled and final concentration of conidia assayed. The reisolates and parent strain were maintained as dried, well-conidiated laboratory solid cultures stored at 4° C. Broth cultures of composition described below were inoculated with conidia from these maintenance culture and incubated at 25° C. on a rotary shaking water bath for three to six days. Broth culture medium resulted in production of high numbers of single-celled blastospores. For some larger cultures, 100 ml of broth culture were transferred to 1.5 liters of broth in 2800 ml flasks incubated at 25° C. with approximately 500 cc/minute sparged air flow.

| Inoculum Culture Medium | |
|---|---|
| Glucose | 40 g/l |
| KNO$_3$ | 10 g/l |
| KH$_2$PO$_4$ | 5 g/l |
| MgSO$_4$ | 1 g/l |
| CaCl$_2$ | 0.05 g/l |
| Yeast Extract | 2 g/l |

Solid culture substrate was prepared by mixing equal parts by weight of dry barley flakes and the inoculum culture medium described above except that glucose was omitted. Wetted barley was autoclaved in polypropylene bags for 20 minutes to one hour (depending on volume) at 15 psi at 121° C., cooled, and inoculated by transferring broth cultures directly to bags of substrate which were mixed. Generally, 1.5 kg dry weight barley flakes were mixed with 1500 ml nutrient solution and autoclaved in one bag, cooled and inoculated with 300 ml of broth culture. Inoculated solid substrate was transferred to an autoclave-sterilized polycarbonate box 27 cm×48 cm×15 cm fitted with a screen bottom and connectors for air inlet and outlet. The substrate formed a bed about eight to ten centimeters deep on the screen. In some cultures, 3 kg dry weight flakes were processed and incubated in 18" diameter×24" deep round steel vessels fitted with screens. The culture beds were about 20 to 30 cm deep. Cultures were incubated at 20–30° C. for 10 days with an air flow of about 0.5 to 2 liters/minute. Air flow was varied to maintain culture temperature. After eight to twelve days incubation, cultures were transferred to a dryer consisting of screens and equipped with a fan. Cultures were spread on screens and dried to a final moisture content of less than 10% with a flow of dry air at 20–25° C.

Dried cultures were passed through a Wiley mill which had cutting blades removed. This removed conidia from dried barley flakes by turbulence and particle to particle abrasion without significantly reducing the size of residual barley flakes. The mill discharged to a covered vibrating mesh screen (US Standard) fitted with a cover. Material that passed through the screen was weighed and assayed for the concentration of viable conidia.

0.1 g conidia preparation was weighed into 9.9 ml 0.1% TWEEN® 80 (tradename for polyoxyethylenesorbitan biological detergent) solution in a Potter-Elvejhem homogenizer tube. The conidia suspension was homogenized for two minutes and diluted as appropriate (generally diluted to certain or estimated 1×10$^6$ to 1×10$^7$ conidia/ml in the final dilution.) Conidia concentration was determined by microscopic count at 400× magnification using a hemocytometer. (Neubauer-Levy or Petroff-Hauser Chamber or equivalent). Viability was determined by placing a drop of diluted conidia suspension on Sabaroud's Dextrose Agar Yeast Extract (SDAY, Difco) plate. The drop was covered with a sterile microscope cover slip and plates were incubated 16–20 hours at 25° C. Plates were examined at 400× and germinated and ungerminated conidia were each counted. Conidia were considered germinated if swollen or if a hypha was emerging from the conidia. Conidia suspensions were sampled in duplicate. For each sample, a total of at least 100 conidia were counted in at least three microscope fields of view. Table 1 below shows labeling, source and spore counts for each isolate.

TABLE 1

Reisolation of BbGH 1991

| Strain | Source Grasshopper | Conidia Concentration | Viability |
|---|---|---|---|
| BbGHA | Lethbridge *Locusta migratoria* | 1.3 × 10$^{11}$ | 90% |
| B | Lethbridge *O. senegalensis* | 9.4 × 10$^{10}$ | 85 |
| C | Cape Verde *O. senegalensis* | 1.3 × 10$^{11}$ | 96 |
| D | | 1 × 10$^{11}$ | 96 |
| E | | 1.4 × 10$^{11}$ | 85 |
| F | | 1.5 × 10$^{11}$ | 96 |
| Parent 201C | | 4 × 10$^{10}$ | 88 |

Conidia production from all reisolates was similar and improved over the parent strain. The six reisolates and parent strain were then compared in laboratory bioassays conducted in cooperation with Agriculture Canada, Lethbridge, Alberta. The first comparison was in a "lettuce disc" assay. In this assay, one centimeter diameter discs were cut from lettuce leaves and treated with two to three microliters of conidia suspension in 0.1% TWEEN® 80 (tradename for polyoxyethylenesorbitan biological detergent) The suspensions were diluted and final volume calculated to supply approximately 1×10$^5$ conidia per disc. Final dilution prior to application to the discs was counted in a microscope hemocytometer. Final conidia dose per disc for reisolates was 9.2×10$^4$ to 1×10$^5$. Discs were allowed to dry for two hours and then placed in individual vials. Grasshoppers—3rd instar *Melanoplus sanguinipes*—were starved 24 hours and then placed in individual tubes with the single lettuce discs. Tubes were held overnight, at which time all grasshoppers had consumed the lettuce discs. Grasshoppers were transferred to one quart clear plastic cups with screen lids and held in a climate-controlled chamber at 25° C. with a 16 hour light, eight hour dark, cycle. Grasshoppers were fed fresh grass and observed for mortality daily. Twenty grasshoppers were treated for each reisolate and parent strain. Table 2 shows cumulative mortality by days post-treatment (day fed). A control group was fed discs treated with TWEEN® 80 (tradename for polyoxyethylenesorbitan biological detergent) solution and no conidia.

TABLE 2

Comparison of Grasshopper Reisolates in Lettuce Disc Bioassay

Cumulative Mortality - # Dead out of 20 treated
Days Post-Treatment

| Reisolate | 4 | 6 | 7 | 8 | 09 | 10 | 11 | 12 | 13 | 14 | 15 |
|---|---|---|---|---|---|---|---|---|---|---|---|
| A | 5 | 12 | 14 | 16 | 18 | 20 | 20 | 20 | 20 | 20 | 20 |
| B | 0 | 5 | 7 | 7 | 8 | 11 | 13 | 14 | 14 | 14 | 14 |
| C | 1 | 9 | 11 | 15 | 17 | 17 | 17 | 18 | 18 | 19 | 19 |
| D | 1 | 4 | 6 | 10 | 12 | 16 | 16 | 16 | 16 | 16 | 16 |
| B | 4 | 11 | 13 | 14 | 15 | 15 | 15 | 15 | 15 | 16 | 16 |
| F | 2 | 7 | 10 | 12 | 13 | 13 | 13 | 13 | 13 | 13 | 13 |
| Parent | 0 | 0 | 0 | 0 | 0 | 13 | 13 | 14 | 15 | 16 | 16 |
| Control | 0 | 0 | 0 | 0 | 2 | 2 | 2 | 2 | 2 | 2 | 2 |

In this assay, reisolate A showed the most rapid kill and the highest final mortality, reaching 100% at 10 days.

Example 2

Conidia Production Efficiency Reisolates

Laboratory solid culture of *Beauveria bassiana* reisolates described in Example 1 were prepared as described above.

Three identical cultures of reisolates BbGHA, BbGHC, BbGHE, and the parent strain were prepared. Reisolates were selected based on virulence shown in Example 1. After 10 days incubation, cultures were assayed for concentration of conidia in whole culture. Table 3 shows the results of the assays.

of conidia remaining on residual culture material after milling and screening also showed considerable conidia concentration, typically on the order of $10^9$-per gram. Based on these observations, total conidia production exceeds $1 \times 10^{13}$ per kg of substrate input.

TABLE 4

Conidia Production B bassiana GHA1991

|  | Set 1 | Set 2 | Set 3 | Set 4 | Set 5 | Set 6 | Set 7 | Total |
|---|---|---|---|---|---|---|---|---|
| 1) Number of Cultures | 14 | 10 | 5 | 8 | 6 | 6 | 7 | 56 |
| 2) Total Substitute Input (kg dry wt) | 25 | 16.5 | 9.0 | 12.0 | 9.0 | 9.0 | 10.5 | 91 |
| 3) Total Recovered Conidia powder (g) | 1964 | 1107 | 703 | 733 | 682 | 809 | 809 | 6807 |
| 4) Total Conidia Recovered | $1.47 \times 10^{14}$ | $7.17 \times 10^{13}$ | $6.48 \times 10^{13}$ | $5.2 \times 10^{13}$ | $5.95 \times 10^{13}$ | $5.75 \times 10^{13}$ | $6.52 \times 10^{13}$ | $5.18 \times 10^{14}$ |
| 5) Average Conidia Concentration Conidia per Gram of Powder | $7.5 \times 10^{10}$ | $6.4 \times 10^{10}$ | $9.2 \times 10^{10}$ | $7 \times 10^{10}$ | $8.7 \times 10^{10}$ | $7.1 \times 10^{10}$ | $7.9 \times 10^{10}$ | $7.6 \times 10^{10}$ |
| 6) Average Conidia Yield Conidia per kg Substrate Input | $5.9 \times 10^{12}$ | $4.3 \times 10^{12}$ | $7 \times 10^{12}$ | $4.3 \times 10^{12}$ | $6.6 \times 10^{12}$ | $6.4 \times 10^{12}$ | $6.2 \times 10^{12}$ | $5.7 \times 10^{12}$ |

TABLE 3

Conidia Per Gram Culture

|  | Average 3 cultures | Average 2 Highest concentration |
|---|---|---|
| A | $1.1 \times 10^{10}$ | $1.5 \times 10^{10}$ |
| C | $1.3 \times 10^{10}$ | $1.4 \times 10^{10}$ |
| E | $5.0 \times 10^9$ | $5.8 \times 10^9$ |
| PARENT | $5.3 \times 10^9$ | $8.4 \times 10^9$ |

Conidia production efficiency of reisolates A and C were superior to E and the parent. Reisolates A and C were approximately equal. Reisolate A was selected as having the best combination of conidia production and virulence. This strain was designated BbGHA1991.

Example 3

Conidia Production Beauveria bassiana Strain BbGHA1991

This example describes production of conidia preparations used in laboratory and field studies described in subsequent examples and demonstrates the consistent high conidia yields obtained with this strain. Solid cultures of BbGHA1991 were prepared and assayed as described in Example 1.

Table 4 summarizes results from 56 cultures with 1.5, 2 or 3 kg dry weight substrate input run in seven separate sets over a 2½ month period. The table shows substrate input, recovered conidia powder, total recovered conidia and calculates conidia yield and concentration. Conidia yield averaged $5.7 \times 10^{12}$ per kg substrate input with an average concentration of $7.6 \times 10^{10}$ conidia/gram. Preparations were pooled and used for laboratory and field tests.

Milling and screening recovered approximately one-half of the conidia produced in the culture. Residual culture material from a number of cultures were remilled and screened with recovery of a quantity of conidia almost equal to the recovery in the first pass shown in the table. Counts Example 4

Virulence in Laboratory Bioassay Topical Application

Conidia powder was prepared from maintenance slants by the method described in Example 1. Conidia powder was suspended in Sunspray 6E oil and serially diluted in oil to achieve final concentrations listed below. Conidia powder mixed with attapulgite clay in a ratio of 1.5 parts conidia powder to 3.5 parts clay was suspended in water and serially diluted in water to the same concentrations as oil suspensions. The clay acted as a suspension aid for the hydrophobic conidia.

Oil and water suspensions were compared in topical bioassay on 3rd instar Senegalese grasshopper, Oedalius senegalensis. In this test, grasshoppers were treated individually with a single 0.25 microliter droplet delivered by microsyringe to the pronotum of the insect. For each dose rate of each formulation, 30 grasshoppers were treated, held individually in small plastic cups, fed daily with fresh, native grass and monitored for mortality.

Doses were 1,000, 10,000, 50,000 and 100,000 conidia in 0.25 microliter per insect. Mortality results are shown in FIG. 1. With the oil suspension, both the rate of kill and final total kill are greater than with the water suspension. The higher mortality rate is particularly significant as there was 90% mortality at six days with the oil formulation compared with 70% using the water suspension. Probit analysis of the data indicates an $LD_{50}$ at 5 days of less than 1000 conidia per insect for an oil formulation.

Example 5

Virulence of BbGHA1991 in Laboratory Bioassay

Laboratory bioassays were conducted on a common pest species of North American grasshopper Melanoplus sanguinipes. Conidia powder was suspended in Sunspray 7N oil and serially diluted in oil so that a 0.2 microliter drop would deliver the following dose range: 100, 390, 1,560, 6,250, 25,000 and 100,000 conidia. For each dose rate, 18–24 insects at 4th instar were treated with a single 0.2 microliter drop to the pronotum, then caged in groups of four to six, fed and monitored daily for mortality. Results are shown in FIG. 2. Probit analysis of the data indicates an $LD_{50}$ at 10 days of about 13,000 conidia per insect.

Example 6

Test of BbGHA1991 on a Non-Target Insect

Oil formulations of BbGHA1991 produced in Example 3 and suspended $2.64 \times 10^9$ conidia/ml in Sunspray® 6E were tested on meal worm (Tenebrio sp.). 30 adult beetles were treated ten at a time using a Paasche airbrush. The airbrush was mounted six feet above the floor and the air pump was set at 25 psi. 0.09 ml of conidia in oil was injected into the airstream of the air brush, spraying insects with a single burst. Oil sensitive cards were laid next to insects to confirm reception of treatment. After treatment, beetles were placed in clear plastic specimen cups along with wheat bran, a small chunk of apple, and crumpled paper towel. Mortality was checked daily. Results of three replicate tests run on different days are shown in Tables 5, 6 and 7. Day number indicates the number of days after beetles were sprayed with BbGHA1991. Numbers in tables represent the number of dead beetles on that day. There were no significant differences among BbGHA1991 treated beetles and controls.

TABLE 5

| Day | 1 | 2 | 3 | 4 | 5 | 6 | 7 | 8 | 9 | 10 | mortality |
|---|---|---|---|---|---|---|---|---|---|---|---|
| Control |  | 1 |  |  |  | 1 | 2 |  | 1 |  | 16.7% |
| 0.09 ml oil | 3 |  |  | 1 |  |  |  |  | 1 |  | 16.7% |
| 0.09 ml B.b. | 2 |  | 1 |  | 1 | 2 |  | 1 | 1 |  | 26.7% |

TABLE 6

| Day | 1 | 2 | 3 | 4 | 5 | 6 | 7 | 8 | 9 | 10 | mortality |
|---|---|---|---|---|---|---|---|---|---|---|---|
| Control | 3 |  |  |  | 2 |  |  |  | 1 |  | 20% |
| 0.09 ml oil | 1 | 1 |  | 2 |  | 1 |  |  | 2 |  | 23.3% |
| 0.09 ml B.b. | 1 | 2 | 1 |  | 1 | 1 |  | 1 | 1 |  | 26.7% |

TABLE 7

| Day | 1 | 2 | 3 | 4 | 5 | 6 | 7 | 8 | 9 | 10 | mortality |
|---|---|---|---|---|---|---|---|---|---|---|---|
| Control | 4 |  |  |  |  |  |  |  | 1 |  | 16.7% |
| 0.09 ml oil | 2 |  |  |  |  |  |  |  |  |  | 6.7% |
| 0.09 ml B.b. | 2 |  |  | 1 |  |  |  | 1 |  |  | 13.3% |

Example 7

Comparative Temperature Stability of BbGHA1991

The temperature stability of BbGHA1991 was compared to a standard strain of Beauveria bassiana ARSEF 252 obtained from the USDA ARSEF culture collection (Ithaca, N.Y.). ARSEF 252 was originally isolated from Colorado Potato beetle.

Stability of unformulated and oil formulated conidia powders were compared in several different experiments. For all experiments, for both strains, conidia powder was produced by methods described in Example 2 for BbGHA1991. Conidia powders were dispensed to screw cap glass vials for tests of unformulated conidia. In formulation tests, conidia powder was suspended in SUNSPRAY® 6N, 6E or 7E oil (light paraffinic oils) to a final concentration of $3 \times 10^9$ to $5 \times 10^9$ conidia per milliliter in 10 ml final volume in screw cap tubes. Tubes were placed in incubators set at the specified temperatures. At selected time intervals, tubes were sampled and assayed for conidia viability according to standard procedures (see Example 1 above and the patent application entitled "A Solid Culture Substrate Including Barley" filed even date herewith, the contents of which are expressly incorporated herein). Results expressed as % viability are described below. (Tables 8, 9, 10)

TABLE 8

Temperature Stability ARSEF 252 - 40° C.
in Sunspray 6 Oil
% Conidia Viability

| Days at 40° C. | Conidia Powder | Sunspray 6E | Sunspray 6N |
|---|---|---|---|
| 0 | 97 | 95 | 95 |
| 5 | 59 | 83 | 83 |
| 7 | 35 | 70 | 70 |
| 12 | <1 | 0 | 0 |
| 14 | 0 | <1 | <1 |

TABLE 9

Temperature Stability BbGHA1991 - 40° C.
% Conidia Viability

| Days at 40° C. | Conidia Powder | Sunspray 6E | Sunspray 6N |
|---|---|---|---|
| 0 | 99 | 99 | 99 |
| 5 | 95 | 95 | 95 |
| 11 | 76 | 90 | 91 |
| 18 | 59 | 80 | 80 |
| 27 | 19 | 10 | 10 |
| 39 | 2 | 2 | 2 |

TABLE 10

Temperature Stability BbGHA and
ARSEF 252 at 25, 32 and 42° C.

| Days in Storage | Dry Powder | | | Oil 7E Formulation | | |
|---|---|---|---|---|---|---|
|  | 25° C. | 32° C. | 42° C. | 25° C. | 32° C. | 42° C. |
| Strain GHA1991 | | | | | | |
| 0 | 99 | 99 | 99 | 99 | 99 | 99 |
| 3 | 99 | 99 | 99 | 99 | 99 | 99 |
| 6 | 99 | 99 | 99 | 99 | 99 | 99 |
| 13 | 99 | 99 | 95 | 99 | 99 | 99 |
| 20 | 99 | 99 | 90 | 99 | 99 | 80 |
| 27 | 95 | 95 | 51 | 95 | 95 | 30 |
| Strain RS 252 | | | | | | |
| 0 | 99 | 99 | 99 | 99 | 99 | 99 |
| 3 | 99 | 99 | 99 | 99 | 99 | 99 |
| 16 | 99 | 99 | 95 | 99 | 95 | 99 |
| 13 | 99 | 99 | 80 | 99 | 99. | 80 |
| 20 | 87 | 85 | 61 | 80 | 90 | <10 |
| 27 | 80 | 25 | 30 | 90 | 85 | <1 |

In all three experiments, with dry powder and formulation in three different oils, BbGHA1991 retained greater viability for longer time ods than ARSEF 252

Example 8

Field Trials of BbGHA1991 in Low Volume Aerial Application

Conidia Preparations, Formulations

Conidia preparations were produced as described in Example 1 above. Conidia preparations were powders, blended to obtain a concentration of $7\times10^{10}$ viable conidia per gram. Conidia were suspended in an oil formulation at a concentration of $2\times10^{12}$ conidia per liter immediately prior to application. Unsprayed oil formulation recovered from the airplane spray tank after application was subsequently stored at room temperature. Dry conidia powder, also stored at room temperature for one year, was added to the original oil formulation to bring the concentration up to $4.5\times10^{12}$ conidia per liter. Conidia were transported to the test sites at ambient conditions as dry powder for first trial and as oil formulation for second trial. Material used in first trial was exposed to transitory temperatures of about 42° C. for about one to two hours as a result of tank circulation in the spray plane. Conidia viability was approximately 95% in preparations used in both trials. Conidia concentrations were determined by hemocytometer count and viability by microscope germination assay as described in Example 1.

Application

Application was by air using an unmodified USDA Cessna "Ag" Truck", equipped with centrifugal pump and standard flat fan spray nozzles (Tee-jet size 8002). Application volume was calibrated by measuring delivery volume of each nozzle tip over 30 seconds in three replicated tests at the selected pump pressure. Aircraft spray time over the plot was recorded by electronic timer. Final application volume was confirmed by the difference in formulation volume in the spray tank before and after application. Application volume in the first trial was 9.3 liters/hectare (one U.S. gallon per acre) and in second trial, 4.6 liters/hectare (two quarts per acre). In both trials, conidia were applied at the rate of $2\times10^{13}$ conidia per hectare ($8\times10^{12}$/Acre). Application was in the early morning with plots sprayed from a height of 10–20 feet. Application coverage was monitored by inspection of oil-sensitive spray cards placed throughout the plots.

Field Sites

Figure 4:
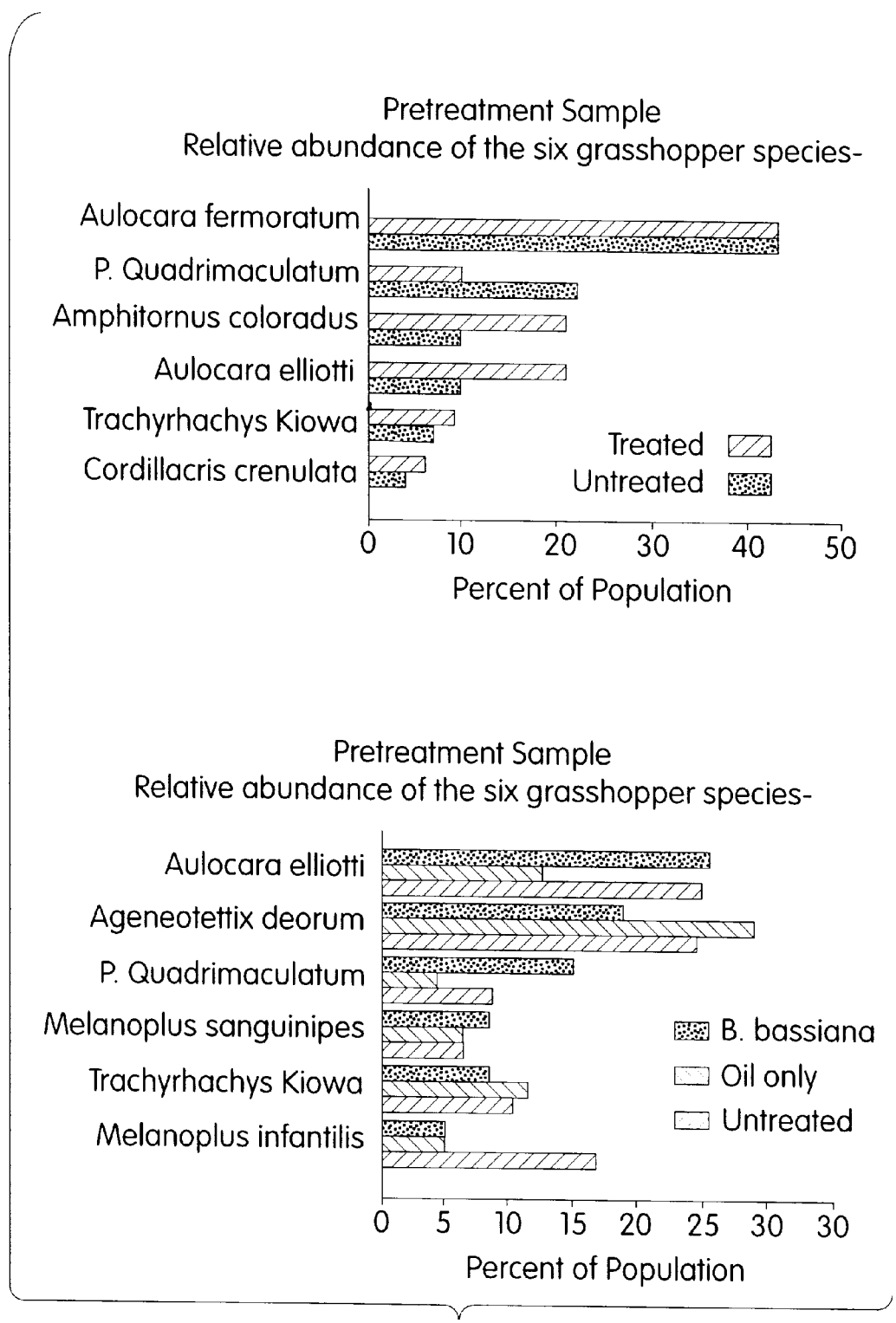
FIG. 4 is bar graphs showing the grasshopper species composition in treated and untreated plots prior to application of BbGHA1991 in low volume aerial application test for two separate tests.

Trials were conducted near Edgemont, South Dakota and near Amidon, North Dakota. Field plots were mixed grass rangeland, typical of improved grazing land in the Western United States. Grasshopper species composition and population age structure were determined from sweep net samples collected two days prior to application. Plots contained a mixed population of grasshopper species and ages. For both trials, the six most abundant species were monitored in efficacy evaluations. These species accounted for about 80% of the total population. Three species were present in both trials. FIG. 4 lists grasshopper species composition in treated and untreated plots prior to application. In each test, application was to a single, 4-hectare (10 acre) plot. Untreated control plots were laid out in adjacent areas with very similar grass mix and grasshopper populations. In second trial, an additional control plot was treated with oil carrier at the same application volume used in test plot.

Efficacy Evaluation

Efficacy was evaluated by three methods: observation of post-treatment grasshopper population samples, grasshoppers caged in the fields, and population density estimates.

For population samples, 50 grasshoppers of each species were collected by sweep net from test, untreated control and oil-only treated control plots. Grasshoppers were held individually in 120 cc plastic cups with screen lids, fed fresh untreated field vegetation supplemented with romaine lettuce and oat cereal and monitored daily for mortality. Cups were held at ambient temperature for 12 days. Mycosis was confirmed by conidiation of *B. bassiana* on grasshopper cadavers. In the first trial, the treated population samples were collected 24 hours after application; in the second trial, the same day as application.

For field cages, 50 grasshoppers of each species were collected from test and from control plots and placed in ten liter cages constructed from plastic buckets and screen. Ten replicate cages with five grasshoppers per cage were used for each species. Treated grasshoppers were placed on treated vegetation and untreated grasshoppers placed on untreated control plots. For tests of infection by exposure to conidia on vegetation, grasshoppers from untreated areas were placed in cages on the treated plots. To isolate effects of direct spray contact, grasshoppers were removed from sprayed plots within one hour after application and held in cages on unsprayed plots. Field population densities were estimated by counts of grasshoppers in $0.1$ $m^2$ rings. In the first trial, eight sample sites with ten rings per site were established in representative types of vegetation cover. In the second trial, plot vegetation was much more uniform and nine sites with ten rings per site were established in a uniform pattern in the plot. Pre-spray grasshopper populations were estimated in counts on the two days immediately prior to application and post-spray counts made at three day intervals.

Results/Discussion

Both population samples (FIG. 5) and field cages (FIG. 6) showed high levels of mortality in treated plots compared with controls for all species in both trials. *Beauveria bassiana* mycosis was confirmed in more than 90% of dead grasshoppers in population samples from treated plots with no evidence of mycosis in dead grasshoppers from control plots.

Time to mortality varied between species with significant mortality beginning in as little as three days for some species and as much as five to six days for other species. One species, *Trachyrhachys kiowa*, showed lower mortality than other species in the first trial but not in the second. These differences could be due to varying susceptibility of different grasshopper species, grasshopper age or behavioral differences that result in varying exposure to conidia.

Figure 7:
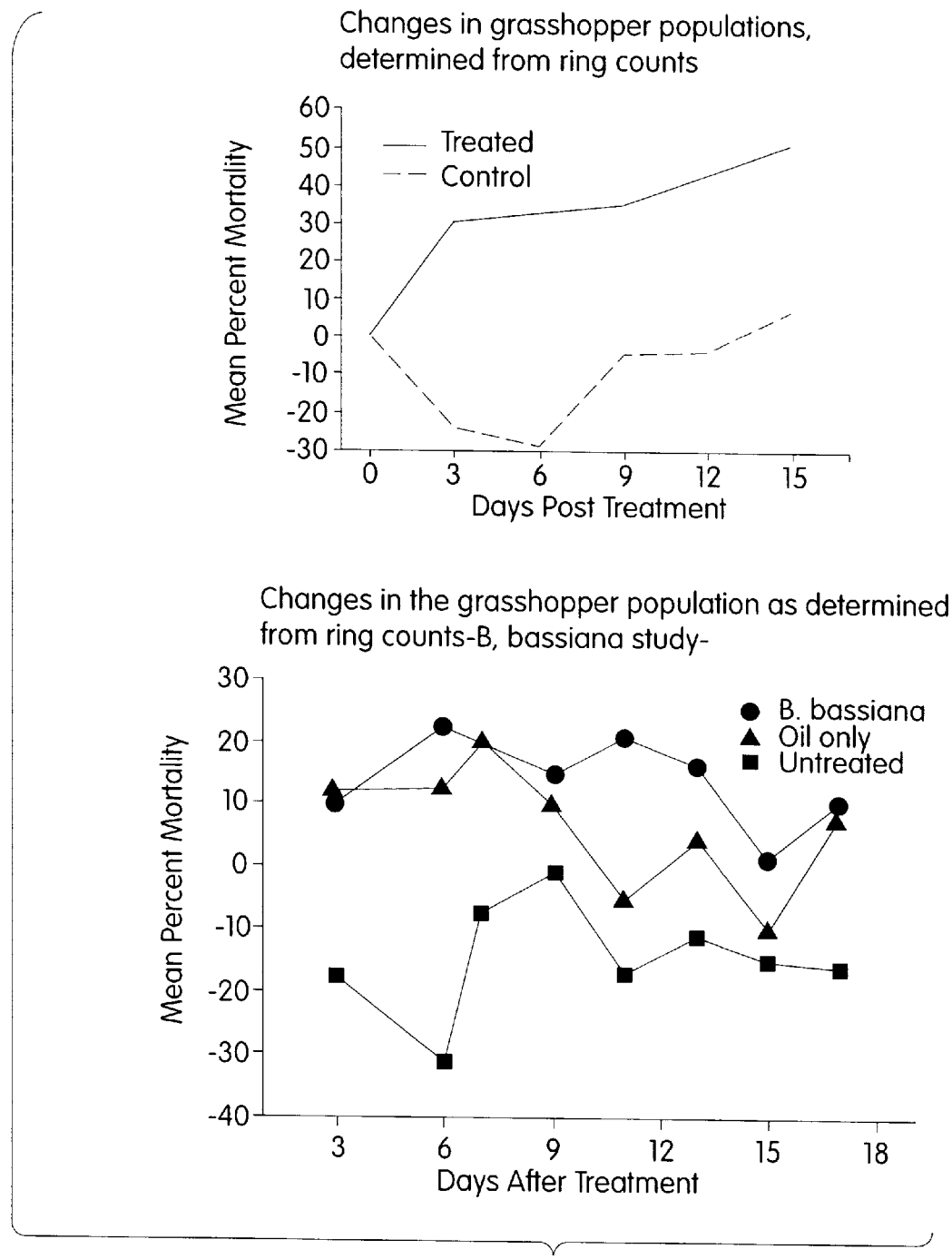
FIG. 7 is graphs showing changes in grasshopper population as determined from ring counts for two separate tests after application of BbGHA1991.

Comparisons of post-treatment population estimates in single, small test and control plots are difficult to interpret. In the first trial, apparent mortality at six days post-treatment was about 60%, but apparent mortality in the second was only about 20–30% after ten days (FIG. 7).

In both trials, significant population increases occurred in control plots with evidence of new hatch in later population samples. Weather was probably a factor in the second trial. Through the first three days post-application, weather was clear with peak afternoon air temperatures of 27–39° C. Between the third and fourth days, a cold front brought rains and cooler temperature through day eight. During this period, peak afternoon temperatures were 9–15° C. with minimums of 4.5–7° C., with intermittently heavy rain. The more rapid mortality of population samples held indoors compared with those grasshoppers in outdoor field cages indicate infection was retarded at cooler temperatures.

Grasshoppers removed from the test plot and placed in cages on unsprayed vegetation showed very high mortality as expected from direct contact by the spray. Tests in which untreated grasshoppers were placed in cages on treated plots demonstrated that exposure to conidia on vegetation can also be a significant source of infection. Table 11 shows mortality at eleven days post-exposure in grasshoppers placed on sprayed vegetation at one hour and ten hours after application. Significant mortality levels were obtained and an infective level of *Beauveria bassiana* conidia remained in vegetation after approximately ten hours of sunlight exposure.

TABLE 11

Comparison of morning and afternoon exposure of the grasshopper *Aulocara femoratum* (Scudder) to a morning aerial application of *Beauveria bassiana*.

| Treatment | Mean percent mortality of eleven days post treatment[b] |
|---|---|
| AM treated | 90 ± 17.0 a |
| PM treated | 96 ± 8.4 a |
| Am untreated | 48 ± 37.9 b |
| PM untreated | 24 ± 20.7 |

[a] Means followed by the same letter do not differ significantly at the 5% level of confidence--Duncan's New Multiple Range Test.
[b] Means ± standard error.

Conclusions

Results obtained in these trials clearly demonstrate very high infection rates in grasshopper populations treated with low volume aerial of oil-formulated *Beauveria bassiana* conidia. These trials have demonstrated efficacy over a very wide range of grasshopper species, vegetation cover, climatic conditions, formulations and application equipment.

Example 9

Field Trial of BbGHA1991—Ground Application

Conidia powder was prepared as described above and transported from Butte, Mont., to Cabo Verde (West Africa) under ambient conditions. Powder contained $7 \times 10^{10}$ conidia per gram.

For ULV application, conidia powder was suspended in Sunspray® 7N oil to a final concentration of $5 \times 10^2$ viable conidia per liter (75 g powder per liter) for application at five liters/ha. Emulsifiable suspension contained 300 g conidia powder in five liters Sunspray® 6E oil. The oil suspension was mixed with 460 g Attaclay RVM and water to a final volume of 20 liters for a one hectare application.

The field test was conducted in cooperation with the Instituto Nacional de Investigacao e Desinvolvimento Agraria (INIDA). INIDA is located at Sao Jorge, Sao Tiago Island, Republic of Cabo Verde. INIDA personnel chose a site three m east of the town of Tarrafal, on the north end of Sao Tiago island. The area was planted with rows of acacia trees, the rows being three to six meters apart. The ground was very rocky with sparse vegetation. The grasshopper population was composed almost entirely of 5th instar larvae and adult *Oedaleus senegalensis*.

A total of nine treatment plots, 100×200 meters (two hectares) each, were laid out with a compass and flagging tape. Three plots were treated with oil-formulated spores, three with emulsifiable suspension-formulated spores, and three were left untreated.

The ULV oil formulation was sprayed at a rate of $2.5 \times 10^{13}$ spores per hectare, in a volume of five liters per hectare, from hand-held Microulva sprayers (Micron Sprayers, Ltd.). The emulsifiable suspension-treated plots also received $2.5 \times 10^{13}$ spores per hectare, but in a volume of 20 liters per hectare. Application was made via gasoline-powered backpack sprayers.

Approximately one hour after treatment, 250 grasshoppers were collected from each plot in sweep nets. These were transported back to the INIDA complex, separated into five cages of 50 grasshoppers each, and maintained in a laboratory. With three plots per treatment, this yielded a total sample of 750 grasshoppers per treatment, or 2250 grasshoppers for the three treatments (oil, emulsifiable suspension, and untreated). Every day, INIDA personnel placed fresh food (grass) in the cages and checked cages for mortality.

Daily grasshopper population density counts were made in the plots by a team of Cape Verde Plant Protection Service technicians using the PRIFAS "visual square meter" method. Each technician walked across a plot, pausing periodically to visually estimate the number of grasshoppers in a square meter. 100 square meters were counted per plot per day, and from this the average number of grasshoppers per hectare was calculated.

Figure 8:
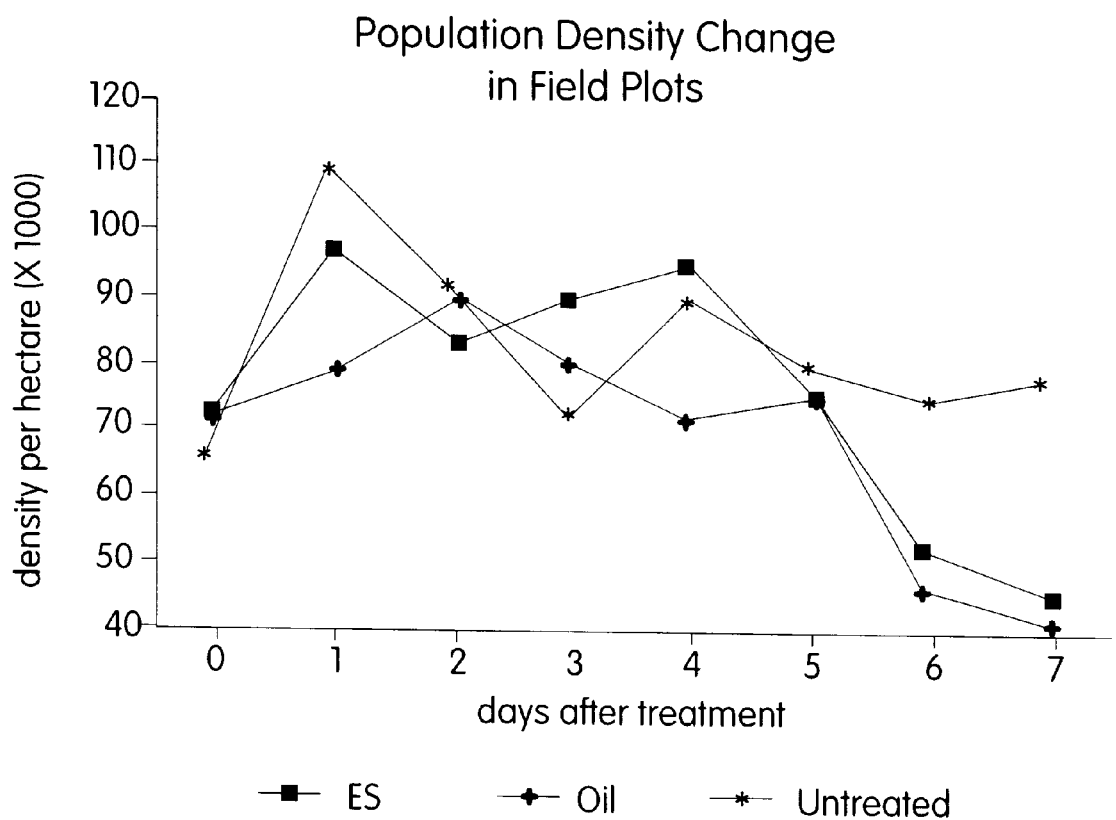
FIG. 8 is a graph showing reduction in grasshopper population density after a ground application test BbGHA1991 and controls.

The reduction in grasshopper population density is shown in FIG. 8. After one week, populations treated with oil-formulated spores were reduced to 57% of untreated controls. ES-treated populations shrank to 54% of untreated. The seven day density reduction is statistically significant for both the oil and ES formulations ($p=0.03$ and $p=0.0204$, respectively).

Figure 9:
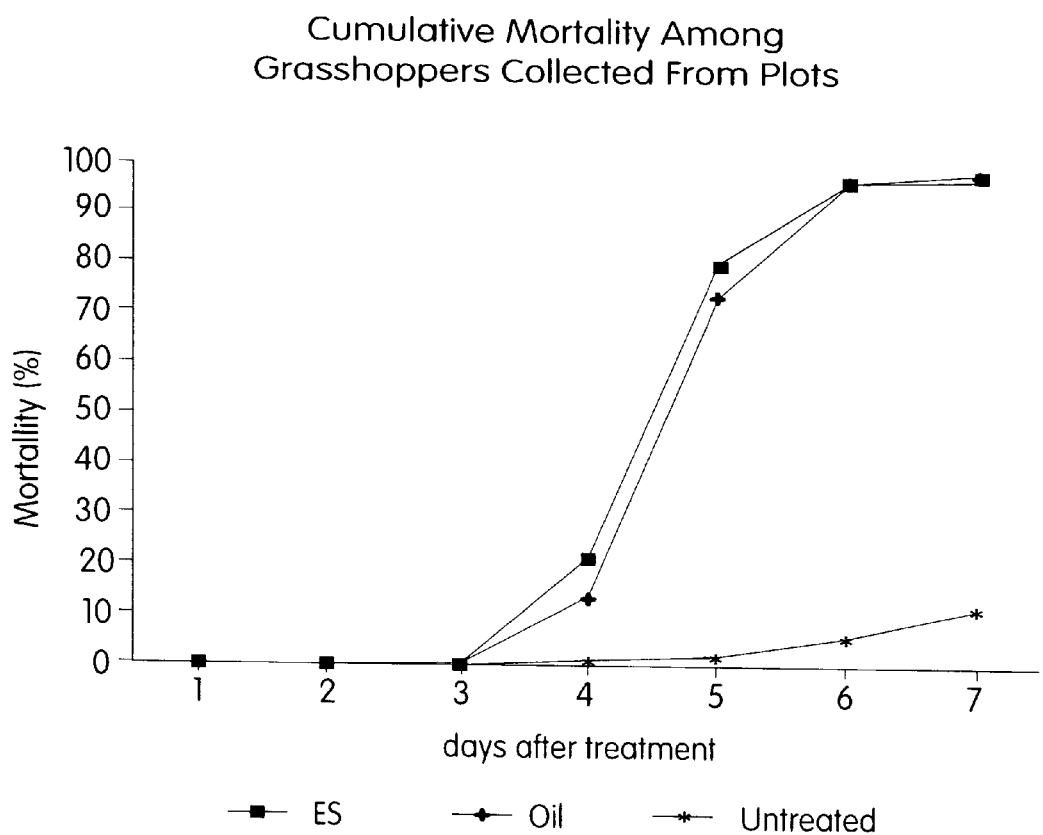
FIG. 9 is a graph showing cumulative mortality of grasshoppers collected one hour post-treatment in a test where the BbGHA1991 and control were applied from the ground.

Cumulative mortality of grasshoppers collected one hour post-treatment is shown in FIG. 9. After seven days, greater than 98% of treated grasshoppers (both oil and ES treatments) were dead, compared with just 12% of untreated controls. Most insects died four to five days after treatment.

Example 10

Field Test of BbGHA1991 Formulated as Wheat Bran Bait

Many grasshoppers are attracted to and preferentially feed on wheat bran. Grasshoppers become infected when feeding on wheat bran coated with BbGHA1991 conidia.

Conidia power prepared as described in Example 1 above was formulated as wheat bran bait and tested in field enclosures on *Oedaleus senegalensis*.

What bran was prepared by mixing dry conidia powder with dry wheat bran in a covered container. A solution of 15% molasses in water was sprayed on the mixture as the mixture was tumbled so as to uniformly moisten the mixture and coat the wheat bran flakes with conidia powder. The mixture was wetted to about 15% final moisture content with the molasses solution. This was sufficient moisture to adhere the conidia powder to the bran flakes but not enough moisture to germinate conidia. The resulting bran bait can be used fresh or redried and stored. When dried molasses aids in adhering conidia to the bran.

The ratio of conidia powder to wheat bran can be varied for different conditions such as application equipment, application rate and grasshopper population density. For the test described in this example, a ratio equivalent to 347 grams conidia powder at $7.2 \times 10^{10}$ conidia per gram on 5 kg wheat bran for application on 1 ha was used. This is equivalent to $2.5 \times 10^{13}$ conidia per ha on 5 kg wheat bran.

The trial was conducted in the Republic of Cape Verde as described in Example 10 at a site in North Central Sao Tingo Island. Tests were conducted in 50 m$^2$ field enclosures constructed of 0.5 m high cloth netting attached to woolen stakes surrounding 5 m×10 m areas of native vegetation. Grasshopper population density in enclosures was approximately 25 3rd and 4th instar *O senegalensis* per m$^2$. Four replicated enclosures were treated with bran bait applied with hand drive granular fertilizer spreaders. Four untreated enclosures were controls. Enclosures served to limit grasshopper migration from plots while providing true field conditions. Twenty grasshoppers were collected from each replicated enclosure 48 hours after application and held in laboratory screen cages, fed fresh grass daily and observed for mortality. Results showing cumulative mortality averaged for the four replicated treated enclosures is shown in Table 12. There was significant grasshopper mortality in BbGHA1991 wheat bran bait treated plots compared with controls.

TABLE 12

Cumulative Mortality in Grasshopper Population Samples From BbGHA1991 Wheat Bran Bait Treated Enclosures

| | Cumulative Mortality % | |
|---|---|---|
| Day Post Exposure | Brain Bait Treated Enclosures | Untreated, Control Enclosures |
| 1 | 0 | 1 |
| 2 | 0 | 1 |
| 3 | 31 | 5 |
| 4 | 63 | 6 |
| 5 | 86 | 13 |
| 6 | 87 | 18 |
| 7 | 90 | 21 |
| 8 | 95 | 25 |
| 9 | 96 | 25 |
| 10 | 96 | 30 |

Example 11

Xylocoris flavipes acute toxicity pathogenicity of *Beauveria bassiana* strain GHA

*Beauveria bassiana* isolate GHA 1991 was evaluated for effects on the pirate bug, *Xylocoris flavipes*. This insect is a predacious species of the order Hemiptera, several other species of which are present in the rangeland habitat of target pest grasshoppers. The study was conducted according to accepted US EPA guidelines.

A stock conidia suspension was prepared by homogenizing 1.24 g conidia power in 10 mi 0.05% TWEEN® 80 (tradename for polyoxyethylenesorbitan biological detergent) for a concentration of $1.7\times10^{10}$ /ml. The stock suspension was serially diluted with water to yield suspensions of $1.7\times10^9$, $1.7\times10^8$ and $1.7\times10^7$ conidia per ml. Twenty microliters of each dilution was applied to 1.41 $cm^2$ filter paper discs to yield application rates of $2.41\times10^7$, $2.41\times10^6$, and $2.41\times10^5$ conidia per $mm^2$. These rates are equal to 100, 10 and 1 times the maximum field rate of $2.5\times10^{13}$ conidia per hectare used in field trials described in Example 10. Heat killed conidia were diluted and applied to discs at the same rate as live conidia for one control. A second control used discs treated with 20 microliters of 0.05% TWEEN® 80 (tradename for polyoxyethylenesorbitan biological detergent) solution.

Treated discs were placed individually in 5 cm×1.5 cm glass vials with forceps. Thirty discs were prepared for each conidia concentration plus controls placed in vials and allowed to dry for one hour. A single, 5th instar *Xylocoris flavipes* was placed in each vial. *Xylocoris flavipes* were obtained from a colony maintained by the Montana State University Entomology Department. *Xylocoris flavipes* were held in vials for ten days, fed daily with larvae of *Tribolium custaneum* (a prey species of *Xylocoris flavipes*) and observed for mortality. In this procedure, *Xylocoris flavipes* is continuously exposed for ten days to *Beauveria bassiana* GHA1991 on the filter paper disc in treated vials.

Table 13 shows mortality of *Xylocoris flavipes* treated with heat killed and viable conidia at the three dose ratio expressed as percent mortality compared with untreated TWEEN® 80 (tradename for polyoxyethylenesorbitan biological detergent solution only) control. At a dose equivalent to the field application rate (assuming a uniform, flat surface), there was no mortality. At 10 and 100 times the field rate, there was 15.7% and 40.8% mortality at day ten. All cadavers in heat killed and live conidia treatments showed *Beauveria bassiana* mycelin after five days in petri dishes maintained at high humidity with damp cotton.

*Beauveria bassiana* GHA1991 showed only a low level of infectivity in *Xylocoris flavipes* at 10 and 100 time field rate or $2.41\times10^6$ or $2.41\times10^7$ conidia per $mm^2$. By comparison, grasshoppers in the lettuce disc bioassay described in Example 1 showed 100% mortality after 10 days when exposed to $1.3\times10^4$ conidia per $mm^2$ or approximately 1850 times less than the 100× exposure rate of *Xylocoris flavipes*.

TABLE 13

Mortality of *Xylocoris flavipes* Exposed to *B. bassiana* strain GHA 1991

| | % Mortality Corrected For Control Mortality | | | | | | | | | |
|---|---|---|---|---|---|---|---|---|---|---|
| | 1 | 2 | 3 | 4 | 5 | 6 | 7 | 8 | 9 | 10 |
| Heat Killed Conidia | | | | | | | | | | |
| $2.41\times10^5/mm^2$ 1× | 0 | 0 | 0 | 0 | 0 | 0 | 0 | 0 | 0 | 0 |
| $2.41\times10^6/mm^2$ 10× | 0 | 0 | 0 | 0 | 0 | 0 | 0 | 0 | 0 | 0 |
| $2.41\times10^7/mm^2$ 100× | 0 | 3.5 | 6.9 | 6.9 | 6.9 | 3.5 | 7.1 | 10.7 | 10.7 | 7.4 |
| Live Conidia | | | | | | | | | | |
| $2.41\times10^5/mm^2$ 1× | 0 | 0 | 0 | 0 | 0 | 0 | 0 | 0 | 0 | 0 |
| $2.41\times10^6/mm^2$ 10× | 0 | 0 | 0 | 10.8 | 14.4 | 15 | 15 | 18.6 | 18.6 | 15.7 |
| $2.41\times10^7/mm^2$ 100× | 0 | 3.5 | 6.9 | 20.7 | 24.2 | 25 | 28.2 | 28.2 | 39.2 | 40.8 |

Example 12

Honeybee Acute Toxicity Pathogenicity of *Beauveria bassiana* strain GHA1991

Effects of *Beauveria bassiana* strain GHA1991 on honeybees was evaluated. This study was conducted under accepted US Environmental Protection Agency rules for Good Laboratory Practice.

Beauveria bassiana GHA1991 preparation was the same lot number as used in Example 5 having an $LD_{50}$ at ten days of about 13,000 conidia per 4th Instar grasshopper *Melanoplus sanguinipes*. Conidia powder and formulation were maintained at 5° C. during storage and transport. Conidia viability was assayed at the time of application according to the method described in Example 1 and was greater than 95%.

Conidia powder was suspended in 0.05% TWEEN® 80 (tradename for polyoxyethylenesorbitan biological detergent) solution using a Potter-Elvejhem cell homogenizer to a concentration of $2.4 \times 10^9$ conidia/ml. Four successive serial dilutions were made in 0.05% TWEEN® 80 (tradename for polyoxyethylenesorbitan biological detergent) to yield suspensions of $5.16 \times 10^8$, $9.9 \times 10^7$, $2.56 \times 10^7$, and $5.56 \times 10^6$ conidia per ml.

Adult worker honeybees (*Apis mellifera*) were treated with a 0.1 microliter drop applied to the mesoscutum with a microsyringe. Thirty bees were treated with each conidia suspension. The 0.1 microliter treatment corresponds to doses of $2.5 \times 10^6$, $6.25 \times 10^5$, $1.56 \times 10^5$, $3.9 \times 10^4$, and $9.8 \times 10^3$ conidia per bee. A control group of bees was treated with suspensions of heat killed (autoclave 15 psi 25 minutes) conidia and a second control group was treated with 1 microliter of 0.05% TWEEN® 80 (tradename for polyoxyethylenesorbitan biological detergent) solution without conidia. Bees were anesthetized with carbon dioxide for treatment.

After treatment, bees were transferred to screen cages and held with daily observation under standard laboratory conditions. *Beauveria bassiana* infection was confirmed by placing dead bees in petri dishes containing water saturated cotton for high humidity and observing development of white conidiating mycelium typical of *Beauveria bassiana*.

Mortality in treated and control groups was recorded and $LD_{50}$ value calculated by probit analysis. Table 14 shows mortality in treated and control groups. $LD_{50}$ at seven days was estimated at $2.0 \times 10^5$ conidia per bee. This is approximately 15 times greater than the grasshopper $LD_{50}$ as shown in Example 5 on *Melanoplus sanguinipes* and 200 times greater than the $LD_{50}$ on *Oedaleus senegalensis* shown in Example 4.

TABLE 14

Mortality in Honeybees Treated Topically with BbGHA1991

| Treatment* | 1 D | 2 D | 3 D | 4 D | 5 D | 6 D | 1 D |
|---|---|---|---|---|---|---|---|
| Control B. bassiana - heat treated - percent corrected mortality | | | | | | | |
| 1 | 0 | 0 | 0 | 3.4 | 0 | 0 | 0 |
| 2 | 0 | 0 | 3.4 | 3.4 | 0 | 0 | 16.6 |
| 3 | 3.3 | 0 | 0 | 0 | 0 | 0 | 3.8 |
| 4 | 3.3 | 3.4 | 3.4 | 3.4 | 0 | 0 | 25 |
| 5 | 3.3 | 0 | 3.4 | 3.4 | 0 | 0 | 3.8 |
| Test B. bassiana - active - percent corrected mortality | | | | | | | |
| 1 | 6.6 | 3.4 | 6.9 | 6.9 | 0 | 41.2 | 66.2 |
| 2 | 0 | 0 | 0 | 6.9 | 0 | 25 | 62.5 |
| 3 | 0 | 0 | 0 | 0 | 0 | 16.2 | 53.8 |
| 4 | 0 | 0 | 0 | 6.9 | 0 | 16.2 | 29.8 |

TABLE 14-continued

Mortality in Honeybees Treated Topically with BbGHA1991

| Treatment* | 1 D | 2 D | 3 D | 4 D | 5 D | 6 D | 1 D |
|---|---|---|---|---|---|---|---|
| 5 | 6.6 | 3.4 | 3.4 | 6.9 | 0 | 0 | 3.8 |

*Treatment: Conidia per bee
1. $2.4 \times 10^6$
2. $5.16 \times 10^5$
3. $9.9 \times 10^4$
4. $2.56 \times 10^4$
5. $5.56 \times 10^3$ Example 13

Effects of *B. bassiana* Strain GHA on *Apthonus flava* (Coleopter:Chrysomelidae)

*Beauveria bassiana* strain GHA1991 was tested for effects on *Apthonus flava*. This insect is a beneficial herbivore which feeds on leafy spurge (*Euphorbia esula* L.), an important noxious weed in rangeland grasshopper habitats. This beetle is being widely introduced in the western U.S. for biocontrol of leafy spurge. It would be a significant advantage for a grasshopper control agent to have less of an effect on *Apthonus flava* and other beneficial herbivores than conventional insecticides under field conditions.

Conidia of *Beauveria bassiana* GHA1991 were suspended in 0.05% TWEEN® 80 (tradename for polyoxyethylenesorbitan biological detergent) to a final concentration of $2.5 \times 10^{10}$ conidia/ml. Conidia were dispersed by use of a Potter-Elvejhem cell homogenizer. This suspension is equivalent to 50× the maximum field rate in 20.0 liters formulation carrier. Conidia concentrations were confirmed by microscope count. Three successive serial dilutions of this suspension were made in 0.05% TWEEN® 80 (tradename for polyoxyethylenesorbitan biological detergent) to yield suspensions of $5 \times 10^9$, $2.5 \times 10^9$ and $5 \times 10^8$ conidia per ml. These are equivalent to 10×, 5× and 1× maximum field rate applied at 20 liters per acre.

Adult *Apthonus flava* were field collected from leafy spurge near Bozeman, Montana. Beetles were maintained on leafy spurge for two to three days before the test. For the test, beetles were divided randomly into five groups of at least 30 beetles per group. Each group was further subdivided into sets of at least ten beetles and placed in holding containers. Three replicates with at least ten beetles per replicate were sprayed with either carrier as control or 50×, 10×, 5× or 1× field rate conidia suspensions. After spraying, beetles were transferred to fresh leafy spurge (with flower heads) in clean plastic containers. Beetles were maintained in test groups at 20–24° C. under natural photoperiod and observed daily for ten days. Fresh food was supplied as necessary. In addition to carrier control, an untreated control was also included.

The spray system was an air brush mounted on a stand and calibrated to deliver the equivalent of 20 liters/acre to a 51 $cm^2$ circular target area. Shallow containers with sets of ten insects were placed in the center of the target area and sprayed with the calculated volume of conidia suspension or carrier. Carrier control was sprayed first, followed by increasing conidia suspensions. Coverage was verified by placing microscope slides in the spray zone with each set of target insects. After spraying, microscope slides were places in 10 ml, 0. 1% TWEEN® 80 (tradename for polyoxyethylenesorbitan biological detergent) in 90 ml plastic tubes, which were shaken, then sonicated to wash off and suspend conidia. Conidia were counted at 400× in a microscope hemocytometer, and conidia per square centimeter of microscope slide calculated. Cumulative mortality was tabulated and $LD_{50}$ at seven and ten days estimated by probit analysis. To confirm mortality due to *Beauveria bassiana*, all dead insects were placed individually in petri dishes containing water agar (15% agar in water), maintained for five days and then examined for *Beauveria bassiana* growth. Results of mortality, confirmed *Beauveria bassiana* infection and actual conidia spray coverage shown in Table 15.

*Beauveria bassiana* strain GHA1991 showed an effect on *Apthonus flava* but at a higher concentrations than used for grasshopper control. Only 10% of beetles were killed at the maximum field rate used in grasshopper control. $LD_{50}$ at seven and ten days is estimated to be $3.1 \times 10^{13}$ and $2.1 \times 10^{13}$ conidia per acre respectively.

TABLE 15

Effects of *Beauveria bassiana* isolate GHA1991 on *Apthonus flava* (Leafy spurge Beetle)

| Days Past Treatment | Cumulative Mortality % | | | | | |
|---|---|---|---|---|---|---|
| | Control Untreated | Control Carrier | 1× | 5× | 10× | 50× |
| 1 | 0 | 0 | 0 | 0 | 0 | 0 |
| 2 | 0 | 0 | 0 | 0 | 0 | 0 |
| 3 | 0 | 0 | 0 | 0 | 3.3 | 0 |
| 4 | 0 | 0 | 3.3 | 0 | 3.3 | 0 |
| 5 | 0 | 0 | 3.3 | 3.3 | 10 | 50 |
| 6 | 0 | 0 | 6.7 | 2.2 | 17 | 72 |
| 7 | 0 | 0 | 10 | 30 | 23 | 81 |
| 8 | 0 | 0 | 10 | 44 | 27 | 84 |
| 9 | 3.3 | 0 | 10 | 52 | 33 | 84 |
| 10 | 6.7 | 0 | 10 | 63 | 37 | 91 |

TABLE 15-continued

Effects of *Beauveria bassiana* isolate GHA1991 on *Apthonus flava* (Leafy spurge Beetle)

| Days Past Treatment | Cumulative Mortality % | | | | | |
|---|---|---|---|---|---|---|
| | Control Untreated | Control Carrier | 1× | 5× | 10× | 50× |
| Cadavers % showing *B. bassiana* | 0 | 0 | 75 | 95 | 91 | 100 |

| conidia dose rate/unitarea | 1× | 5× | 10× | 50× |
|---|---|---|---|---|
| conidia/cm² | $2.2 \times 10^5$ | $3 \times 10^5$ | $7.7 \times 10^5$ | $2.4 \times 10^5$ |
| conidia/acre | $0.9 \times 10^{13}$ | $1.2 \times 10^{13}$ | $3.1 \times 10^{13}$ | $9.1 \times 10^{13}$ |

EQUIVALENTS

Those skilled in the art will recognize, or be able to ascertain using no more than routine experimentation, numerous equivalents to the specific embodiments described herein. Such equivalents are considered to be within the scope of this invention and are covered by the following claims.

We claim:

1. A biologically pure culture of a strain of an entomopathogenic fungus which has all The identifying characteristics of *Beauveria bassiana* strain BbGHA1991.

2. A biologically pure culture of *Beauveria bassiana* strain BbGHA1991. ATCC 74250.

3. An entomopathogenic formulation comprising a fungus of any one of claims 1 or 2 and a carrier.

4. An entomopathogenic formulation comprising conidia of a fungus of any one of claims 1 or 2 and a carrier.

* * * * *

UNITED STATES PATENT AND TRADEMARK OFFICE
CERTIFICATE OF CORRECTION

PATENT NO. : 5,939,065
DATED : August 17, 1999
INVENTOR(S) : Bradley et al.

It is certified that error appears in the above-identified patent and that said Letters Patent is hereby corrected as shown below:

At column 24, line 28, delete "The" and insert --the--.
At Column 24, line 31, delete "." and insert --,--.

Signed and Sealed this

Seventh Day of March, 2000

Attest:

Attesting Officer

Q. TODD DICKINSON
Commissioner of Patents and Trademarks